United States Patent [19]
Tehrani

[11] Patent Number: 4,960,585
[45] Date of Patent: Oct. 2, 1990

[54] RAPID HAIR PH INDICATION AND SOLUTION THEREFOR

[76] Inventor: Nasser N. Tehrani, 9 Drum Hill La., Stamford, Conn. 06902

[21] Appl. No.: 476,331

[22] Filed: Feb. 7, 1990

Related U.S. Application Data

[63] Continuation-in-part of Ser. No. 317,774, Mar. 2, 1989, abandoned.

[51] Int. Cl.$^5$ ............................ A61K 7/06; A61K 9/20
[52] U.S. Cl. ............................................ 424/7.1; 8/405; 8/406; 424/62; 424/70; 424/71; 424/72; 424/73
[58] Field of Search .................................. 424/7.1, 70

[56] References Cited

U.S. PATENT DOCUMENTS 4,313,393  2/1982  Barbuscio et al. .................. 116/200

FOREIGN PATENT DOCUMENTS 2919422  11/1980  Fed. Rep. of Germany .......... 424/7

OTHER PUBLICATIONS

*Chemical and Physical Behavior of Human Hair,* 1979, 1st Edition, Van Nostrand Reinhold, pp. 95, 96, 110 and 111, Robbins.

*Primary Examiner*—Dale R. Ore
*Attorney, Agent, or Firm*—Parmelee, Bollinger & Bramblett

[57] ABSTRACT

A solution for the rapid indication of hair pH and method of determining hair pH and restoration of hair to its isoionic range with buffered conditioning rinses.

36 Claims, No Drawings

RAPID HAIR PH INDICATION AND SOLUTION THEREFOR

RELATED APPLICATION

This Application is a Continuation-In-Part of my earlier copending Application Ser. No. 07/317,774 filed Mar. 2, 1989 now abandoned.

FIELD OF THE INVENTION

This invention relates to a method for indicating the pH of hair and to an indicator solution for such method. The invention further relates to a method of indicating the pH range of hair and to the use of buffered conditioning rinses to restore the hair pH to or maintain hair within its isoionic range of pH 6 to 7 and preferably to the isoionic point of about pH 6.4.

BACKGROUND TO THE INVENTION

Human hair is comprised of the protein keratin, a hard, horny, fibrous material which consists of long, tapering fibrillar cells that have coalesced and contain about 16.6 to 18% of the amino acid cystine. The structure of the hair comprises an outer cuticle, a main portion called the cortex and often a central medulla.

The hair shaft or cortex is covered by a layer of thin, outer, colorless scales forming the cuticle. This layer of scales has the appearance of overlapping roof tiles with their free ends directed toward the tip of the hair. The main portion of the hair shaft, the cortex, comprises very closely packed longitudinally arranged spindle shaped cells and fibers firmly attached to each other. These cells and fibers contain air bubbles and pigment (melanin) that gives color to the hair. The medulla, if present, is a loose arrangement of axial fibers and angular cells containing air bubbles. The color of the hair is due to the pigment in the cortical cells and light reflected from the central medulla.

The protein of the hair consists of amino acids, linked peptide fashion with each other with the amino groups of one amino acid molecule linked to the carboxyl group of another amino acid molecule. However, this linkage can be broken by the action of concentrated solutions of strong alkalis or acids and also by certain enzymes. In addition, the keratin molecules are strengthened by so-called hydrogen linkages. When the hair is caused to swell, these bonds are weakened and are broken by certain concentrated salt solutions.

The weakening and/or destruction of these bonds is detrimental to the health and vitality of the hair. Alkalis and acids reduce or nullify the mechanical and chemical strength of this hair protein. In an alkaline medium, water causes a discernible swelling of the hair protein and the polypeptide chains are pushed apart. As the pH value rises higher into the alkaline range, the greater the degree of this swelling of the hair shaft. As a result, the scales of the cuticle laminae are pushed apart and may even become detached from the fibrous shaft. This action leads to further damage to the hair since alkali can now penetrate directly into the horny protein. Application of strong alkaline solutions at elevated temperatures can lead to the hair being dissolved. Moreover, hair having a pH in the alkaline range generally is dull and lusterless. Weak aqueous acids, while desirably closing the cuticular laminae of the hair to prevent undesirable penetration thereof, can also result in the formation of undesirable neutralization salts. Acids also split the salt-type cross linkage found in the hair. Strong acids damage the hair and stronger acids, below pH 2, destroy hair. Additionally weathering effects, i.e. damage to hair by environmental factors, such as by sunlight, sea water, chlorinated pool water and air pollutants, such as acid rain, chemically alter hair, which alterations can be detected at the morphological level.

These effects have provided the basis for many treatments of the hair. That is, the opening of the cuticle scales and exposure of the cortex by alkalis has enabled the formulation of various alkaline preparations for various treatments of hair. For example, bleaching preparations of pH 9.5 to 10; hair tints or dyes of pH 8 to 1; waving preparations of pH 8 to 10; hair straighteners of pH 11 to 12; and shampoos or shaving soaps of pH 8 to 10 have been formulated to take advantage of that phenomena. Similarly, acid preparations such as fixatives or neutralizers of pH 2.5 to 4.0; peroxide hair lighteners of pH 2.5 to 3.0; hair setting agents of pH 4.5 to 7.0 and shampoos of pH 5 to 7 have been formulated to take advantage of the effect of acid solution on hair.

However, hair has greater strength and resiliency when in its isoionic region, i.e. when at a pH of from about 6.0 to 7.0; and its greatest strength and resiliency when at or near its isoionic point of about pH 6.4—the isoionic point reported by Steinhardt and Harris, J. Res. Nat. Bur. Stand. 24, 335–367 (1940). The pH at which a protein or a particle has an equivalent number of positive and negative charges which arise exclusively from proton exchange is the isoionic point. The isoionic point is a whole-fiber property of hair and is reflected by the equilibrium acid-base properties of the total hair fiber. For long-term interactions, if the pH of a surrounding solution is below the isoionic point of hair, the hair will pick up acid, and above its isoionic point, it will attract hydroxide ions more readily. The isoionic point therefore becomes more important to whole-fiber treatments such as perms, bleaches, straighteners and hair dyes. When outside the isoionic range, hair is easily broken upon combing, brushing or teasing or other similar treatments. The cuticles have an increased ability to withstand wear when hair is in the isoionic range and thus hair is able to grow longer due to fewer loss of cuticles.

The various alkali and acid formulations employed to obtain various effects upon the hair, such as those mentioned hereinbefore, have led to hair often being outside its isoionic range, i.e. either in the alkaline range above or the acid range below the isoionic range. Buffered rinses or conditioners have been utilized to treat such alkaline or acid pH hair in an attempt to bring the hair pH back to or close to its isoionic range. However, the use of such rinses or conditioners have been on a chance or guesswork basis, i.e. by rinsing with a buffered acid rinse or conditioner after undergoing an alkali treatment such as bleaching or tinting, or by rinsing with a buffered alkali rinse or conditioner after undergoing an acid treatment such as peroxide hair lighteners. However, such chance treatment may or may not bring the hair back to its desired isoionic range.

It is therefore highly desirable that a formulation and process be available to rapidly and easily determine if hair is within its isoionic range or outside said range, and if outside the range whether outside on the acid or alkaline side. This would enable one to knowingly use the appropriate buffered rinse or conditioner to restore hair to within its isoionic range and preferably to the isoionic point of about pH 6.4.

SUMMARY OF THE INVENTION

A process for the rapid and easy determination of the pH range of hair and a pH indicator solution for accomplishing same is provided by this invention. According to the invention, a hair pH indicator solution is provided which produces a first color for hair having an acid pH within the isoionic range of pH from about 6.0 to 7.0, a second and different color for hair having an acid pH of below about pH 6, and a third and different color for hair having an alkaline pH of above pH 7. In this manner, hair treated with the indicator solution will provide a distinctive color indication if the hair is in the acid range below about pH 6, within the isoionic range of about pH 6 to 7, or within the alkaline range above pH 7.

Any combination of pH indicators which will provide these distinctive, different colors for the three aforesaid hair pH ranges can be employed in the indicator solution of this invention provided the resulting solution meets the other criteria set forth hereinafter. As example of such suitable indicator solutions, there may be mentioned a solution of methyl red and bromthymol blue or a solution of alizarin red S and bromthymol blue. An indicator solution of methyl red and bromthymol blue is preferred.

Hair, in an appropriate indicator solution of methyl red and bromthymol blue will turn the solution red or yellow if the hair is strongly or weakly acidic, respectively, below pH 6; will turn the solution green if the hair is within the isoionic range of pH 6 to 7; and will turn the solution blue if the hair is alkaline, above pH 7. Similarly, hair in an appropriate indicator solution of alizarin red S and bromthymol blue will turn the solution yellow or red if the hair is strongly or weakly acidic, respectively, below pH 6; will turn the solution green if the hair is within the isoionic pH range of pH 6 to 7; and will turn the solution blue if the hair is alkaline, above pH 7.

While any indicators that provide an indicator solution which turns three distinctive differing colors within the three aforesaid pH ranges can be employed, it is necessary for the indicator solution to have a conductivity, at a temperature of about 20°–22° C., of at least about 10,000 ohms or more, preferably at least about 20,000 ohms or more, and most preferably a conductivity of at least about 50,000 ohms or more, generally within the range of from 50,000 to 100,000 ohms.

The solution of indicators of the aforesaid conductivity can be provided, for example, by employing deionized or triple distilled water generally of a conductivity of 1 meg. ohms and sufficient indicator to provide the differential color formation without compromising the conductivity of the solution. For example, on a percent weight/weight (% wt/wt) basis, a suitable indicator solution would contain from about 0.0002 to about 0.003% bromthymol blue and from about 0.00001 to about 0.0002% methyl red, preferably about 0.0025 bromthymol blue and about 0.0001 methyl red. Similarly, a suitable indicator solution can be formed utilizing appropriate amounts of other suitable indicators.

It is often desirable that the indicator solution also have present other components to enhance or preserve the activity of the indicator solution. For example, since the presence of any undesirable metal ions would be deleterious to the indicator solution, a suitable chelating agent, such as for example, disodium EDTA or the like, may be employed in an effective metal chelating amount. Similarly, an antioxidant and/or preservative, such as for example, propyl paraben, may be added in an effective antioxidant and/or preserving amount. Since methyl red is readily subject to oxidation, it is preferred that an antioxidant such as propyl paraben or methyl paraben be present in such an indicator solution containing methyl red to enhance the shelf life and sunlight stability of the indicator solution. The amount of chelating agent, preservative or antioxidant present in the indicator solution can be any effective amount so long as the conductivity of the solution meets the aforesaid parameter.

The pH indicator solutions of this invention will generally have a pH of about 6 to 6.5 and adjustment of the pH of the indicator solution to within this pH range can be made by addition of an appropriate amount of an appropriate acid or base solution, e.g. 1N HCl, or 1N NaOH.

The indicator solutions of this invention are generally prepared, for example, by adding the ingredients, preferably one at a time, to deionized or triple distilled water of suitable conductivity in an appropriate mixing vessel. Such a mixing vessel and its propeller will be sterile, non-metallic and non-glass, and is preferably plastic. The ingredients are mixed completely and dissolved in the water.

As an example of a preferred indicator solution of this invention there may be mentioned, for example, the following exemplary formulation:

| Component | % wt/wt |
|---|---|
| Deionized water | 99.9939 |
| Bromthymol blue | 0.0025 |
| Methyl red | 0.0001 |
| Disodium EDTA | 0.0025 |
| Propyl paraben | 0.0010 |
| | 100.0000 |

Said formulation has a conductivity of 50,000 ohms resistance at a temperature of 22° C.

Said exemplary indicator solution will produce the following colors for the indicator solution in the presence of hair of the designated pH.

TABLE

| Hair pH | Solution color shade |
|---|---|
| 4–5 | Dark Orange/Red-Light Orange/Red |
| 5–6 | Dark Yellow-Light Yellow |
| 6–7 | Light Green-Dark Green |
| 7–9 | Light Blue-Dark Blue |

As an example of the use of the indicator solution according to this invention, there may be mentioned the following preferred exemplary procedure using the aforementioned exemplary formulation. A small amount of hair, generally about 0.2 g., is placed into a suitable container, free of metallic ions, preferably a plastic test tube, to which an appropriate amount of indicator solution is then added. For example, about 3.5 ml of indicator solution is added to a 10 ml plastic test tube to cover the 0.2 g. sample of hair. After capping the test tube, the tube is shaken vigorously for a few seconds until a color change is visible. A red or yellow colored solution is noted if the hair pH is acidic, i.e. below the isoionic range; a blue colored solution is noted if the hair pH is alkaline, i.e. above the isoionic range; and a green colored solution is noted if the hair is in the isoionic range of pH 6 to 7. Although an indicator solution color is generally visible within a few seconds, it is generally preferred to wait for one minute or two before the final hair pH color determination is made.

After determining the hair pH, one is provided with the necessary information to determine the type of buffered rinse or conditioner to use on the hair to restore to or retain the hair within the isoionic pH range of pH 6 to 7 and preferably to the isoionic point of about pH 6.4. For example, if the hair pH is acid (yellow or red solution color), the following exemplary buffered rinse solution of pH 7.0 would be applied to the acidic hair:

| BUFFERED RINSE FOR ACIDIC HAIR | |
|---|---|
| Component | % wt/wt |
| Deionized water | 99.49 |
| Sodium dibasic phosphate | 0.32 |
| Sodium monobasic phosphate | 0.19 |
| | 100.00 |

For convenience sake, this buffered rinse for acid hair could be colored yellow or red to coordinate with the color of the pH indicator solution when in the presence of hair of acidic pH.

If the hair pH is alkaline, the following exemplary buffered rinse solution of pH 6.0 could be applied to the hair:

| BUFFERED RINSE FOR ALKALINE HAIR | |
|---|---|
| Component | % wt/wt |
| Deionized water | 99.49 |
| Sodium dibasic phosphate | 0.08 |
| Sodium monobasic phosphate | 0.43 |
| | 100.00 |

Similarly, for convenience sake, this buffered rinse for hair of alkaline pH could be colored blue to coordinate with the color of the indicator solution when in the presence of hair of alkaline pH.

If the hair is already within the isoionic range of pH 6 to 7, a buffered rinse of pH about 6.4 to 6.5 of the following exemplary formulation could be applied to the hair to maintain the hair within isoionic pH range of pH 6 to 7:

| BUFFERED RINSE FOR ISOIONIC RANGE HAIR | |
|---|---|
| Component | % wt/wt |
| Deionized water | 99.49 |
| Sodium dibasic phosphate | 0.18 |
| Sodium monobasic phosphate | 0.33 |
| | 100.00 |

This buffered rinse for hair within the isoionic pH range could be colored green to coordinate with the color of the indicator solution when in the presence of hair of this isoionic pH range.

It is not necessary to use the above mentioned exemplary buffered rinse solution since any suitable buffered rinse or conditioner solution may be used to restore or maintain the hair pH within the isoionic range of pH 6 to 7 and preferably to the isoionic point of about pH 6.4. The foregoing buffered solutions have been set forth merely as examples of such solutions suitable for use. Other such buffered rinse solutions are known or readily prepared and could be employed.

By the use of the indicator solution of this invention one may readily and easily determine the pH range of a hair sample and then treat hair accordingly with the appropriate buffered rinse or conditioner to restore or maintain the hair pH to a pH within the isoionic range of pH 6 to 7 and preferably to the isoionic point of about pH 6.4.

I claim:

1. A method for the determination of the pH of a hair sample to determine if the hair pH is within the hair isoionic range of about pH 6 to 7 comprising contacting the hair sample with a pH indicator solution for a period of time sufficient for the indicator solution to change to a color indicative of the hair being within one of three pH ranges, said solution changing to a first color when the hair pH is within the hair isoionic range of about pH 6 to 7, to a second and different color when the hair pH is acidic and below about pH 6 and to a third color different from the first and second colors when the hair pH is alkaline above about pH 7.

2. The method of claim 1 wherein the indicator solution used in the method has a conductivity of about 10,000 or more ohms at about 20° C.

3. The method of claim 2 wherein the conductivity of the indicator solution is about 50,000 or more ohms.

4. The method of claim 1 wherein the indicator solution comprises an aqueous solution of a color indicating pH effective amounts of bromthymol blue and methyl red.

5. The method of claim 2 wherein the indicator solution comprises an aqueous solution of a color indicating pH effective amounts of bromthymol blue and methyl red.

6. The method of claim 3 wherein the indicator solution comprises an aqueous solution of a color indicating pH effective amounts of bromthymol blue and methyl red.

7. The method of claim 4 wherein the indicator solution also comprises a metal chelating effective amount of a metal chelating agent.

8. The method of claim 4 wherein the indicator solution also comprises an antioxidant effective amount of an antioxidant agent.

9. The method of claim 7 wherein the indicator solution also comprises an antioxidant effective amount of an antioxidant agent.

10. The method of claim 5 wherein the indicator solution also comprises a metal chelating effective amount of a metal chelating agent.

11. The method of claim 5 wherein the indicator solution also comprises an antioxidant effective amount of an antioxidant agent.

12. The method of claim 10 wherein the indicator solution also comprises an antioxidant effective amount of an antioxidant agent.

13. The method of claim 9 wherein the chelating agent comprises disodium EDTA and the antioxidant comprises propyl paraben.

14. The method of claim 12 wherein the chelating agent comprises disodium EDTA and the antioxidant comprises propyl paraben.

15. The method of claim 13 wherein the indicator solution comprises on a percent wt/wt basis:

| deionized water | about | 99.9939% |
|---|---|---|
| bromthymol blue | about | 0.0025% |
| methyl red | about | 0.0001% |
| disodium EDTA | about | 0.0025% |

| -continued | | |
|---|---|---|
| propyl paraben | about | 0.0010% |

16. The method of claim 14 wherein the indicator solution comprises on a percent wt/wt basis:

| deionized water | about | 99.9939% |
|---|---|---|
| bromthymol blue | about | 0.0025% |
| methyl red | about | 0.0001% |
| disodium EDTA | about | 0.0025% |
| propyl paraben | about | 0.0010% |

17. An indicator solution for the determination of whether a hair sample has a pH within the hair isoionic range of about pH 6 to 7 comprising a pH indicator solution which in contact with a hair sample changes to a first color when the hair pH is within the hair isoionic range of about pH 6 to 7, to a second and different color when the hair pH is acidic and below about pH 6 and to a third color different from the first and second colors when the hair pH is alkaline above about pH 7.

18. The indicator solution of claim 17 wherein the indicator solution has a conductivity of about 10,000 or more ohm at about 20° C.

19. The indicator solution of claim 18 wherein the conductivity of the indicator solution is about 50,000 or more ohms.

20. The indicator solution of claim 17 wherein the indicator solution comprises an aqueous solution of a color indicating pH effective amounts of bromthymol blue and methyl red.

21. The indicator solution of claim 18 wherein the indicator solution comprises an aqueous solution of a color indicating pH effective amounts of bromthymol blue and methyl red.

22. The indicator solution of claim 19 wherein the indicator solution comprises an aqueous solution of a color indicating pH effective amounts of bromthymol blue and methyl red.

23. The indicator solution of claim 20 wherein the indicator solution also comprises a metal chelating effective amount of a metal chelating agent.

24. The indicator solution of claim 20 wherein the indicator solution also comprises an antioxidant effective amount of an antioxidant agent.

25. The indicator solution of claim 23 wherein the indicator solution also comprises an antioxidant effective amount of an antioxidant agent.

26. The indicator solution of claim 21 wherein the indicator solution also comprises a metal chelating effective amount of a metal chelating agent.

27. The indicator solution of claim 22 wherein the indicator solution also comprises an antioxidant effective amount of an antioxidant agent.

28. The indicator solution of claim 26 wherein the indicator solution also comprises an antioxidant effective amount of an antioxidant agent.

29. The indicator solution of claim 25 wherein the chelating agent comprises disodium EDTA and the antioxidant comprises propyl paraben.

30. The indicator solution of claim 28 wherein the chelating agent comprises disodium EDTA and the antioxidant comprises propyl paraben.

31. The indicator solution of claim 29 wherein the indicator solution comprises on a percent wt/wt basis:

| deionized water | about | 99.9939% |
|---|---|---|
| bromthymol blue | about | 0.0025% |
| methyl red | about | 0.0001% |
| disodium EDTA | about | 0.0025% |
| propyl paraben | about | 0.0010% |

32. The indicator solution of claim 30 wherein the indicator solution comprises on a percent wt/wt basis:

| deionized water | about | 99.9939% |
|---|---|---|
| bromthymol blue | about | 0.0025% |
| methyl red | about | 0.0001% |
| disodium EDTA | about | 0.0025% |
| propyl paraben | about | 0.0010% |

33. A method for returning hair to or maintaining hair within the hair isoionic pH range of about pH 6 to 7 comprising:
contacting a sample of said hair with sufficient pH indicator solution for a period of time sufficient for the indicator solution to change to a color indicative of hair being within one of three pH ranges, said pH indicator solution changing to a first color when the hair pH is within the hair isoionic range of about pH 6 to 7, to a second and different color when the hair pH is acidic and below about pH 6 and to a third color different from the first and second colors when the hair pH is alkaline above about pH 7, and
after determining the pH range of the hair treating the hair with a buffered rinse solution, said buffered rinse solution being buffered pH rinse solution of pH about 6.0 when the hair sample produces a color indication of alkaline hair pH, said buffered rinse solution being a buffered pH rinse solution of about pH 7.0 when the hair sample produces a color indication of acidic hair pH and said buffered rinse solution being a buffered pH rinse solution of pH about 6.4 to 6.5 when the hair sample produces a color indication of the hair sample being within the hair isoionic range of about pH 6 to 7.

34. The method of claim 33 wherein, on a percent wt/wt basis:
the buffered rinse solution of pH 7.0 comprises:

| deionized water | about | 99.49% |
|---|---|---|
| sodium dibasic phosphate | about | 0.32% |
| sodium monobasic phosphate | about | 0.19% | the buffered rinse solution of pH 6.0 comprises:

| deionized water | about | 99.49% |
|---|---|---|
| sodium dibasic phosphate | about | 0.08% |
| sodium monobasic phosphate | about | 0.43% | and
the buffered rinse solution of pH 6.4 to 6.5 comprises:

| deionized water | about | 99.49% |
|---|---|---|
| sodium dibasic phosphate | about | 0.18% |
| sodium monobasic phosphate | about | 0.33% |

35. The method of claim 34 wherein the buffered rinse solution of pH about 6.0 is a blue colored solution, the buffered rinse solution of pH about 7.0 is a yellow colored solution and the buffered rinse solution of pH about 6.4 to 6.5 is a green colored solution.

36. A method of claim 33 wherein the method returns or maintains hair at about the isoionic point of pH 6.4.

* * * * *

UNITED STATES PATENT AND TRADEMARK OFFICE
CERTIFICATE OF CORRECTION

PATENT NO.   : 4,960,585

DATED        : October 2, 1990

INVENTOR(S)  : Nasser Norman TEHRANI

It is certified that error appears in the above-identified patent and that said Letters Patent is hereby corrected as shown below:

Column 2, line 13, "to 1" should read "to 11".

Signed and Sealed this

Twenty-fifth Day of February, 1992

Attest:

HARRY F. MANBECK, JR.

*Attesting Officer*       *Commissioner of Patents and Trademarks*